United States Patent
Hoy

(10) Patent No.: US 12,016,822 B2
(45) Date of Patent: Jun. 25, 2024

(54) BACK BRACE WITH REPOSITIONABLE PRESSURE NODULES

(71) Applicant: Kevin Hoy, Sagamore Hills, OH (US)

(72) Inventor: Kevin Hoy, Sagamore Hills, OH (US)

( * ) Notice: Subject to any disclaimer, the term of this patent is extended or adjusted under 35 U.S.C. 154(b) by 898 days.

(21) Appl. No.: 15/958,034

(22) Filed: Apr. 20, 2018

(65) Prior Publication Data

US 2020/0268589 A1   Aug. 27, 2020

(51) Int. Cl.
*A61H 7/00* (2006.01)
*A61F 5/02* (2006.01)
*A61F 5/30* (2006.01)

(52) U.S. Cl.
CPC ............. *A61H 7/002* (2013.01); *A61F 5/028* (2013.01); *A61F 5/30* (2013.01); *A61H 2201/0107* (2013.01); *A61H 2201/1261* (2013.01); *A61H 2201/1623* (2013.01); *A61H 2201/1647* (2013.01); *A61H 2201/165* (2013.01); *A61H 2205/081* (2013.01)

(58) Field of Classification Search
CPC ............. A61F 5/028; A61H 2205/081; A61H 2201/165
See application file for complete search history.

(56) References Cited

U.S. PATENT DOCUMENTS

| | | | | | |
|---|---|---|---|---|---|
| 3,605,731 | A | * | 9/1971 | Tigges | F16K 31/02 128/845 |
| 4,159,020 | A | * | 6/1979 | von Soiron | A61F 5/26 601/1 |
| 4,175,548 | A | | 11/1979 | Henry | |
| 5,127,897 | A | | 7/1992 | Roller | |
| 5,290,307 | A | | 3/1994 | Choy | |
| 5,560,046 | A | * | 10/1996 | Iwamasa | A61F 5/028 128/101.1 |
| 5,885,230 | A | | 3/1999 | Cherry | |
| 6,214,027 | B1 | * | 4/2001 | Brossard | A61H 7/001 602/19 |
| 8,795,214 | B1 | * | 8/2014 | Conti | A61F 5/028 602/19 |
| 2004/0055076 | A1 | | 3/2004 | Yoo | |
| 2013/0030337 | A1 | * | 1/2013 | Anglada | A61F 5/028 602/19 |
| 2015/0011921 | A1 | * | 1/2015 | Sidhu | A61H 39/04 601/134 |

(Continued)

OTHER PUBLICATIONS

Carolyn Sayre, "12 Ways to Improve Back Pain", WebMD.com, https://www.webmd.com/back-pain/features/12-back-pain-tips#1.

(Continued)

*Primary Examiner* — LaToya M Louis
(74) *Attorney, Agent, or Firm* — Hudak, Shunk & Farine Co. LPA

(57) ABSTRACT

A system of placeable and removable pressure nodules is provided having different types of size and configuration and having a density semi-soft, to rigid. The nodules are removably attachable and affixable into a back brace modified and adapted to implement SMRT. Precise, specialized, and individualized pressure is provided to the muscles, tendons, and connective tissues through the nodules in order to alleviate any need for manual massage. The user's own active motions (bending, twisting, walking) engages the muscles and massage the muscles with the pressure nodules.

3 Claims, 6 Drawing Sheets

(56) References Cited

U.S. PATENT DOCUMENTS

2015/0342774 A1* 12/2015 Dudkiewicz ............ A61F 5/028
                                                    602/19
2018/0028396 A1*  2/2018 Brodsky ................ A61H 15/00

OTHER PUBLICATIONS

Cone Health, "Back Injury Statistics," Jul. 2012, https://localtvwghp.files.wordpress.com/2012/07/back-injury-and-surgery-statistics.pdf.
Peter Grickej, "How Does a Back Brace Work? What You Need to Know," Posturebly, Jul. 1, 2014, http://posturebly.com/how-does-a-back-brace-work-what-you-need-to-know.
Stacy Peny, "Foam Rolling—Applying The Technique of Self-Myofascial Release," NASM.org, Aug. 21, 2013, http://blog.nasm.org/training-benefits/foam-rolling-applying-the-tech.
Leonid Kalichman, et al., "Effect of self-myofascial release . . . " Journal of Body and Movement Therapies, Apr. 2017, vol. 21, Issue 2, p. 446-451.
"Accupressure Points and Massage Treatment," WebMD.com, https://www.webmd.com/balance/guide/acupressure-points-and-massage-treatment#1.

* cited by examiner

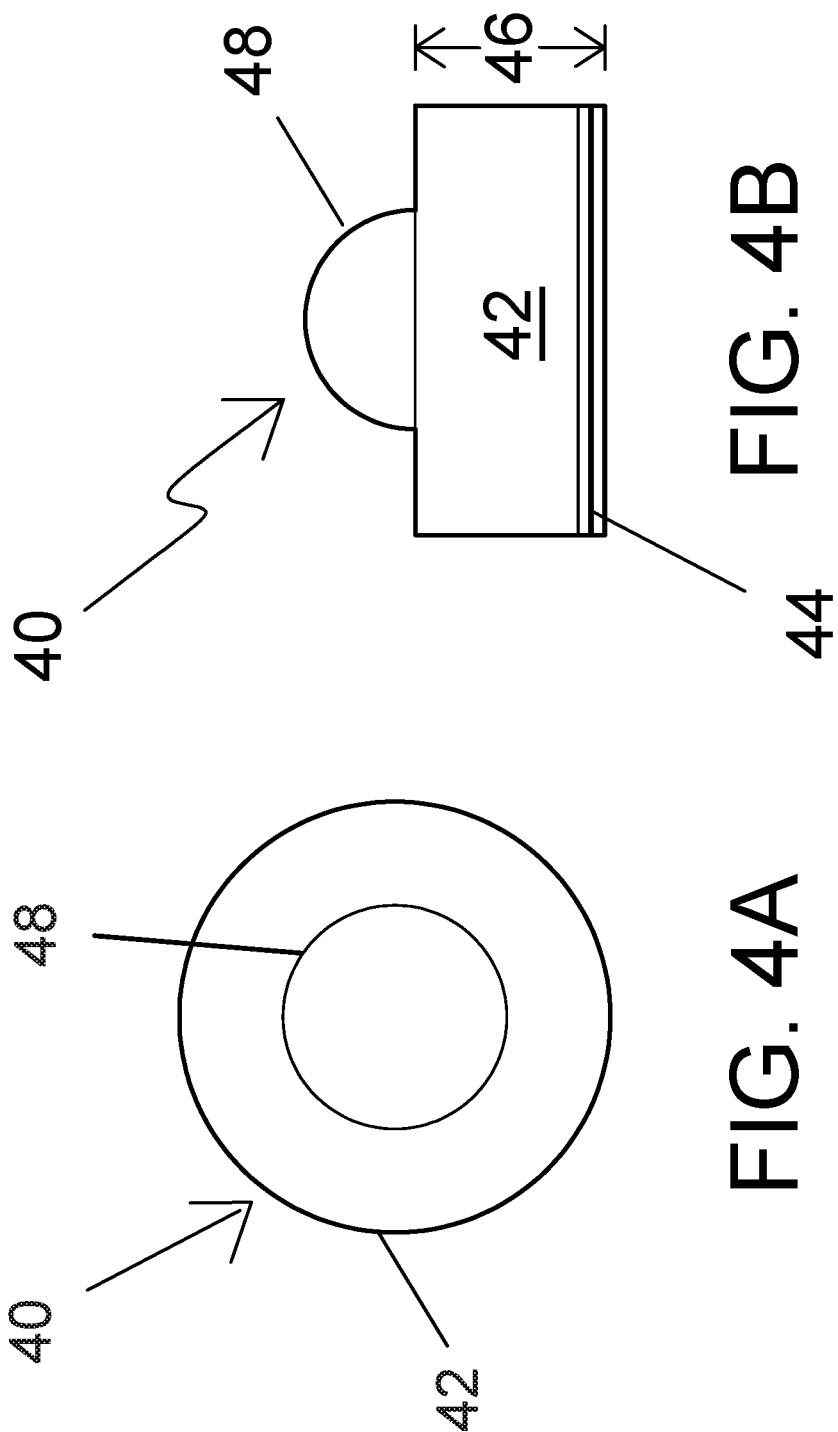

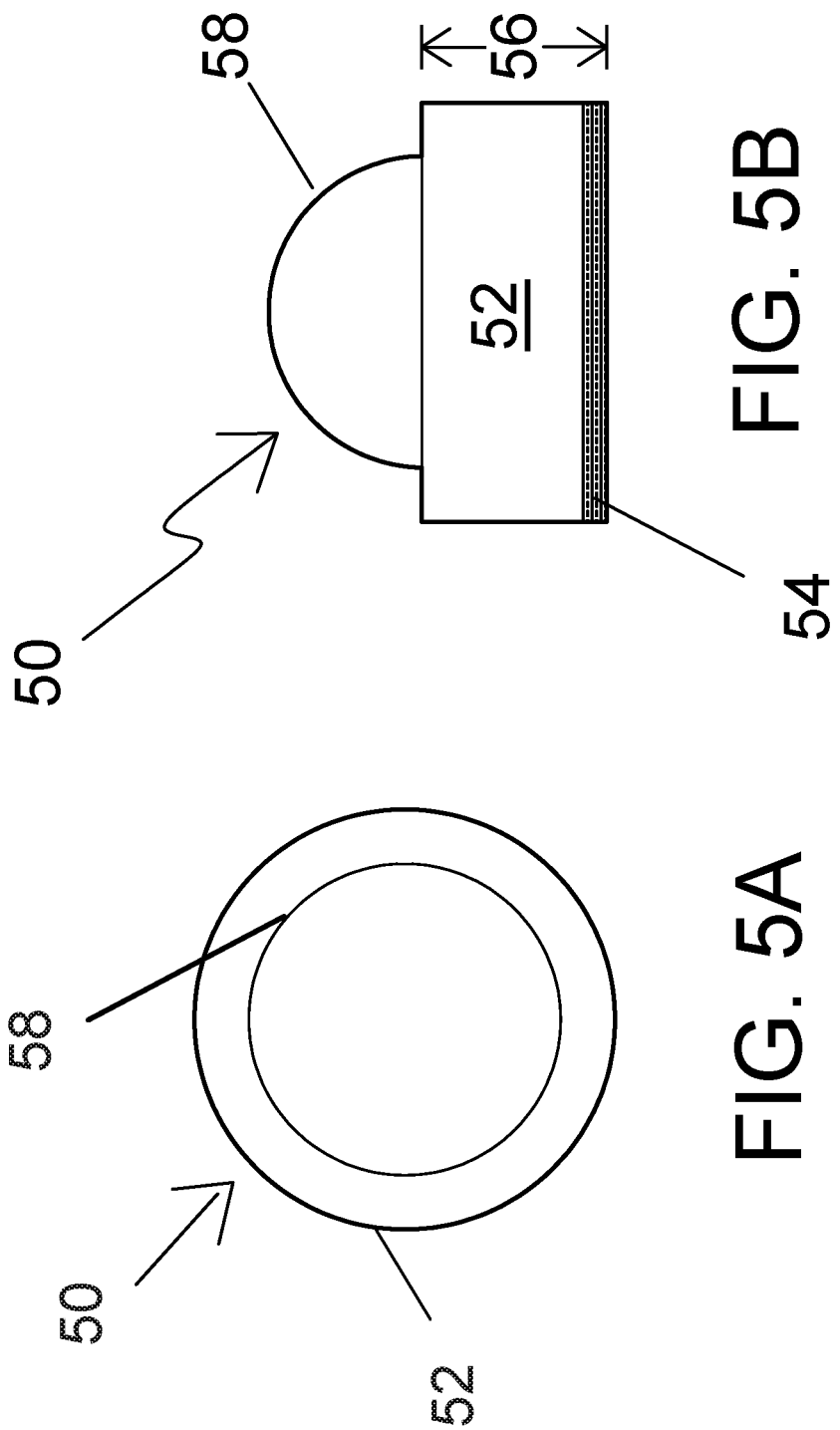

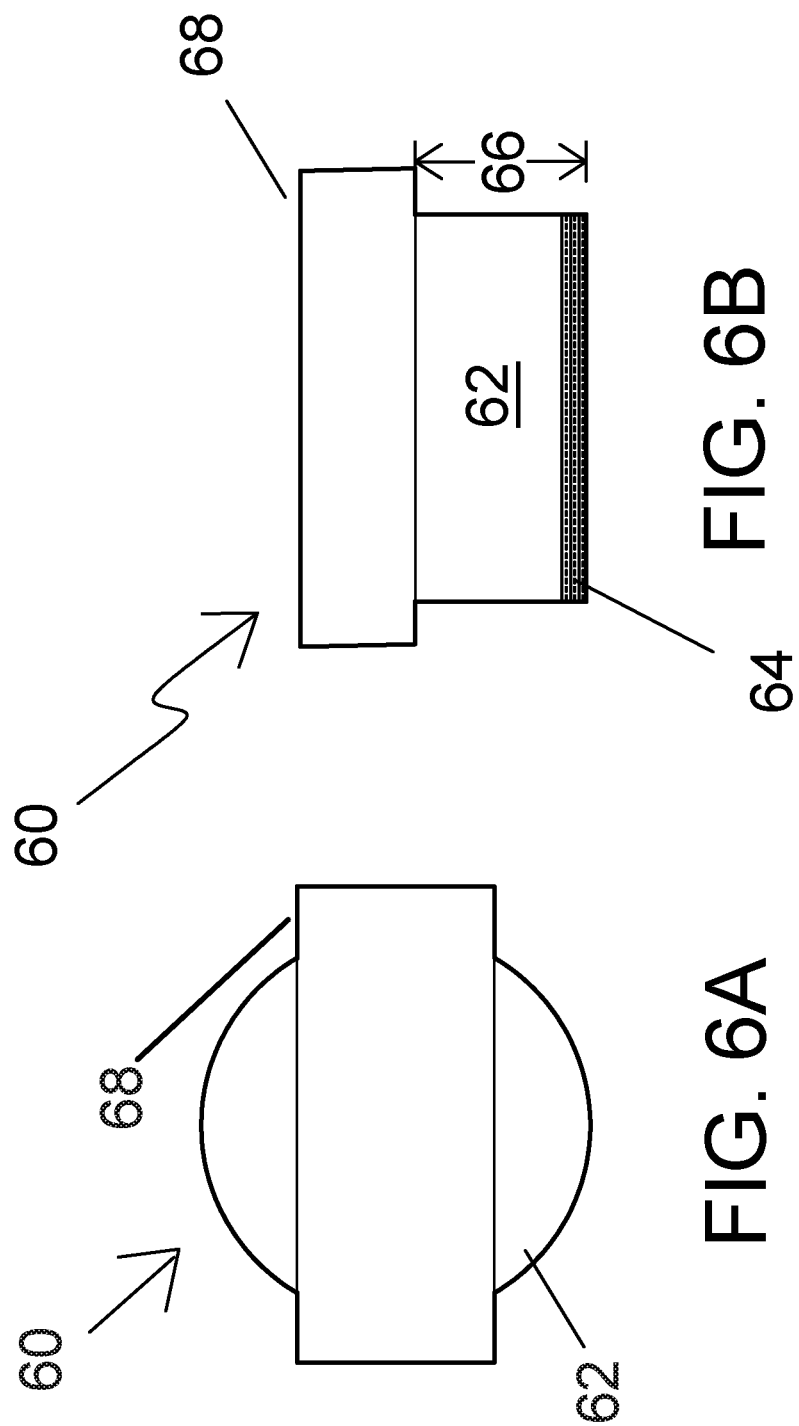

BACK BRACE WITH REPOSITIONABLE PRESSURE NODULES

BACKGROUND OF THE INVENTION

1. Field of the Invention

The present invention relates generally to support braces and, more particularly, to back support braces.

2. Description of the Related Art

As many as 80% of Americans will experience a back injury during their lifetime, see Carolyn Sayre, "12 Ways to Improve Back Pain", WebMD.com, https://www.webmd.com/back-pain/features/12-back-pain-tips #1. Of those, 10% are likely to suffer a re-injury to the back, see Cone Health, "Back Injury Statistics," July 2012, https://localtvwghp.flies.wordpress.com/2012/0?/back-injury-and-surgery-statistics.pdf. Because of this, back injuries are the biggest justification for workplace absenteeism, even more prevalent than the common cold.

In the face of these common, and often times crippling, injuries, back braces have become increasingly popular. Back braces seek to minimize or thoroughly eliminate back pain by supporting muscles and bones located in the lower back, as well as by limiting the range of motion in the spine, see Peter Grickej, "How Does a Back Brace Work? What You Need To Know," Posturebly, Jul. 1, 2014, http://posturebly.com/how-does-a-back-brace-work-what-you-need-to-know. There are two popular types of back braces, corset braces and rigid braces. Corset braces limit motion by prohibiting the user from bending forward or backward. Rigid braces, on the other hand, are more form-fitting and limit motion by 50%.

Back braces are effective because they help to stabilize the spine and supports and encourages proper posture. Nevertheless, back braces can be uncomfortable and put unnecessary, and often times painful, pressure on the user's abdomen.

In the realm of manual interaction, one technique for relieving back pain is the use of acupressure therapy. This technique finds its roots in bodywork therapies used by the ancient Asian societies, see "Accupressure Points and Massage Treatment; webMD.com, https://www.webmd.com/balance/guide/acupresure-points-and-massage-treatment #1. (IDS Ref. 6) This traditional Chinese theory leverages so-called "acupoints" within the body which lie along channels; these channels are identical to those used in acupuncture. (Id.) Acupressure works by having a massage therapist manually apply light pressure to these "acupoints" across the body. (Id.)

Another manual technique to alleviate back pain is the use of self-myofascial release techniques ("SMRT"). Perhaps the most popular rendition of SMRT is the iconic foam roller. Other applications of SMRT are embodied in medicine balls, handheld rollers, and other assistive devices. SMRT works to hone in on neural and facial systems within the body, as these areas are more prone to negative influence from bad posture, repetitive motions, and painful motions, see Stacy Peny, "Foam Rolling-Applying The Technique of Self-Myofascial Release," NASM.org, Aug. 21, 2013, http://blog.nasm.org/training-benefits/foam-rolling-applying-the-tech. SMRT benefits the body by, among other benefits, correcting imbalances within the muscles, relaxing the muscles, improving range of motion within the joints, reducing soreness, and decreasing the stressful effects of one's movements. (Id.) Researchers have observed "significant increase in the joint range of motion after using the [SMRT] technique and no decrease in muscle force or changes in performance after treatment." See Leonid Kalichman, et al., "Effect of self-myofascial release . . . " Journal of Body and Movement Therapies", April 2017, Vol. 21, Issue 2, pg 446-451.

U.S. Pat. No. 5,290,307 to Choy, entitled Spinal Acupressure Device, discloses an acupressure belt for the treatment of lower back pain formed of a central fabric panel to which opposed elastic panels are affixed. The elastic panels terminate in a pair of end panels which may be joined together to retain the belt about the torso of the wearer. Located on the inner surface of the central panel is a plurality of acupressure-applying protrusions, each of which are individually positionable on the panel. The protrusions are positioned to apply pressure to the L1-L4 acupressure points associated with the lower spine. A pair of overlapping elastic panels are further affixed to the opposed sides of the control panel about the torso with the protrusions in position, whereby acupressure is generated and applied for the relief of lower back pain. Notably, Choy only discloses buttons that are "spherical segments . . . on the order of ⅝ inch diameter and ½ in height". Furthermore, this device uses stiffeners and teaches a perimeter welting running around the perimeter of the central panel. Such structural elements would inherently diminish this device's ability to stretch in the plane of the central panel.

U.S. Pat. No. 5,470,304 to Decanto, entitled Apparatus and Method for Providing Pressure Point Therapy, discloses a belt for providing individual pressure points in a user's lower back region in order to alleviate back pain. The belt is secured about the waist and includes a main panel positioned against the lower back region. The main panel includes several apertures corresponding to possible points of therapy. Threaded pins are inserted into the apertures corresponding to a point in the lower back where pain is being experienced. The pins are rotated through the main panel into the lower back thus providing pressure to the point of interest in the lower back. The pressure can be adjusted by rotation of the pin as desired. However, the only position adjustment is through inserting of pins into alterative preformed apertures, and no pin geometries are disclosed for focusing or defocusing pressure.

U.S. Pat. No. 5,127,897 to Roller, entitled Therapeutic Back Support Device, discloses a back support device for use in applying force to vertically opposite sides of the spine at any selected one of a plurality of different vertical levels. While providing rigid places used as force concentrating members, this device does not teach or suggest a resilient central panel having hook and loop mounted pressure nodules.

U.S. Pat. No. 4,175,548 to Henry, entitled Massage Back Brace, provides a massage back brace having a resilient arrangement mounted on a flexible support member and covered by a resilient pad. The brace is affixable in position on a wearer's back by a belt-like strap removably attachable to the flexible support member and fastened together about a wearer's torso. However, this reference is silent regarding structure that could be construed as a positionable pressure nodule of any kind.

U.S. Pat. No. 5,885,230 to Cherry, entitled External Gastroesophageal Valve Closer, discloses device and method relate to closing a users gastroesophageal valve to prevent acid reflux from the users stomach. The device includes a belt having an inner surface and at least one fastener, the belt being sized to fit around an upper abdominal area of the user. A pliable triangular insert contains a gel material, the insert being attachable to the inner surface of the belt and sized to fit over the triangular area between the ribs and directly below the breast bone of the user. The insert conforms to the shape of the users body and imparts pressure to the upper abdominal area of the user over the users lower esophagus and gastroesophageal valve when the belt is tightly fastened around the user.

U.S. Patent Publication US2004/0055076 to Yoo, entitled Belt for Acupressure, provides an elastic textile belt for acupressure, including securing elements at opposite ends of the belt for securing the belt around the waist of a user; an abdominal acupressure element having a plurality of metal protrusions on the inner surface of the belt and a pouch for holding heat generating elements on an outer surface of the belt; a movable lumbar acupressure element having a plurality of metal protrusions on the inner surface, a plurality of hooks on the outer surface and a pouch for holding heat generating elements between the surfaces.

It is preferable that a back brace be modified and adapted to implement SMRT into the brace functionality by incorporating a system of placeable and removable pressure nodules. Through this system of nodules, the user can place the nodules anywhere over the lower back and sacral regions. This provides precise, specialized, and individualized pressure to the muscles, tendons, and connective tissues of each individual. Through this, the brace would decrease the need for the user to manually massage the area of pain. Such a system would leverage the users own active motions—such as bending, twisting, or walking—to engage the muscles and massage the muscles with the pressure nodules. This brace would further include a strapping system, which the user can adjust to provide the desired pressure. To reduce pressure on the abdomen, this strapping system should be attached near the anterior hip region. This brace should provide an active cut designed to allow for freer motion of the hips and thighs, thus preventing the brace from riding up while the user is walking or sitting.

SUMMARY OF THE INVENTION

It is thus an object of the present invention to provide a superior back brace to leverage aspects of SMRT, by utilizing a system of placeable and removable pressure nodules to apply individualized pressure to the muscles, tendons, and connective tissues of the lower back and sacral regions.

It is a feature of the present invention to provide a system of placeable and removable pressure nodules, which allows the user to place the nodules as they desire, to provide specialized and individualized pressure to the muscles, tendons, and connective tissues of the user's lower back and sacral regions.

It is a feature of the present invention to provide a quad pull strapping system to allow the user to adjust the pressure applied to particular nodules. Specifically, a lower strap can be adjusted to increase or decrease the pressure over the sacral and lower back regions, while an upper strap can be adjusted to increase or decrease the pressure to the uppermost part of the lower back region. These straps will attach near the anterior hip region, thus providing less pressure on the user's abdomen.

It is a feature of the present invention to provide an active cut design. This active cut design would allow for free motion of the user's hips and thighs, thus preventing the back brace from riding up whenever the user walks or sits.

The present invention provides a system and method for providing pressure individualized by the user to specific areas of the sacral and lower back regions, thus providing back pain relief similar to effective SMRT techniques, rather than simply preventing motion and encouraging proper posture.

Further objects, features, elements and advantages of the present invention will become readily apparent from the following detailed description of the preferred embodiment when considered with the attached drawings and the appended claims.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

FIG. 4a is a side elevational view of a pressure nodule 40 according to a first configuration for use in conjunction with the present invention;

FIG. 4b is a top plan view thereof;

FIG. 5a is a side elevational view of a pressure nodule 50 according to a second configuration for use in conjunction with the present invention;

FIG. 5b is a top plan view thereof;

FIG. 6a is a side elevational view of a pressure nodule 60 according to a third configuration for use in conjunction with the present invention; and FIG. 6b is a top plan view thereof.

DESCRIPTION OF THE PREFERRED EMBODIMENTS

Figure 1:
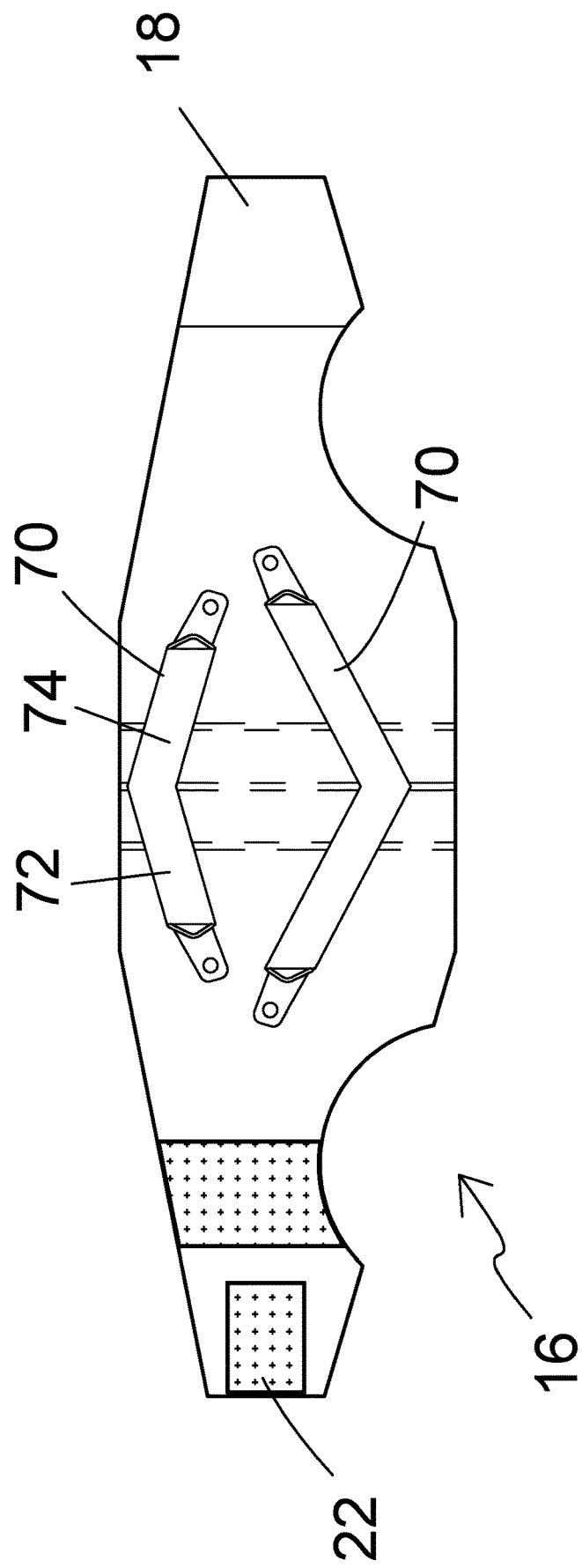
FIG. 1 is a front elevational view of a back support brace according to the preferred embodiment of the present invention.
Figure 2:
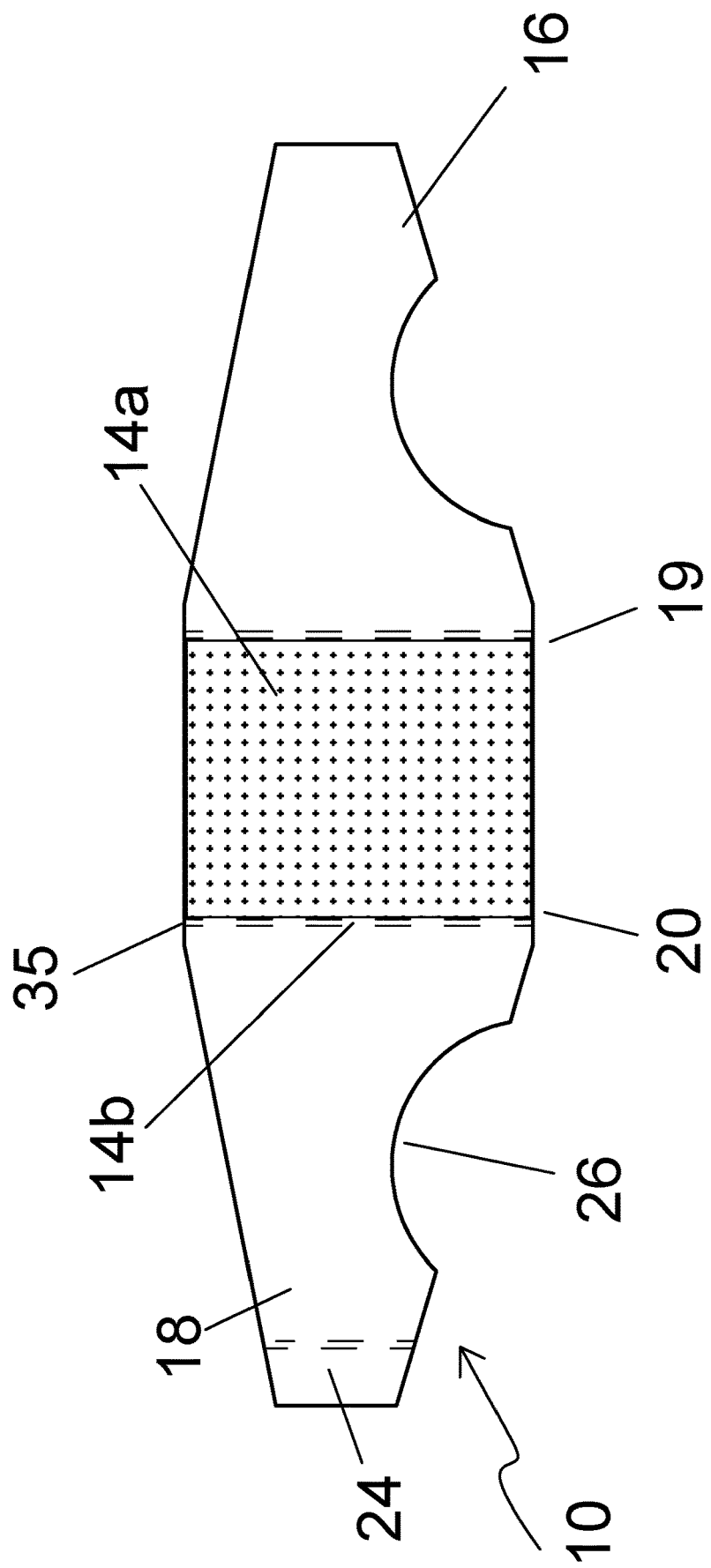
FIG. 2 is a rear elevational view thereof.
Figure 3:
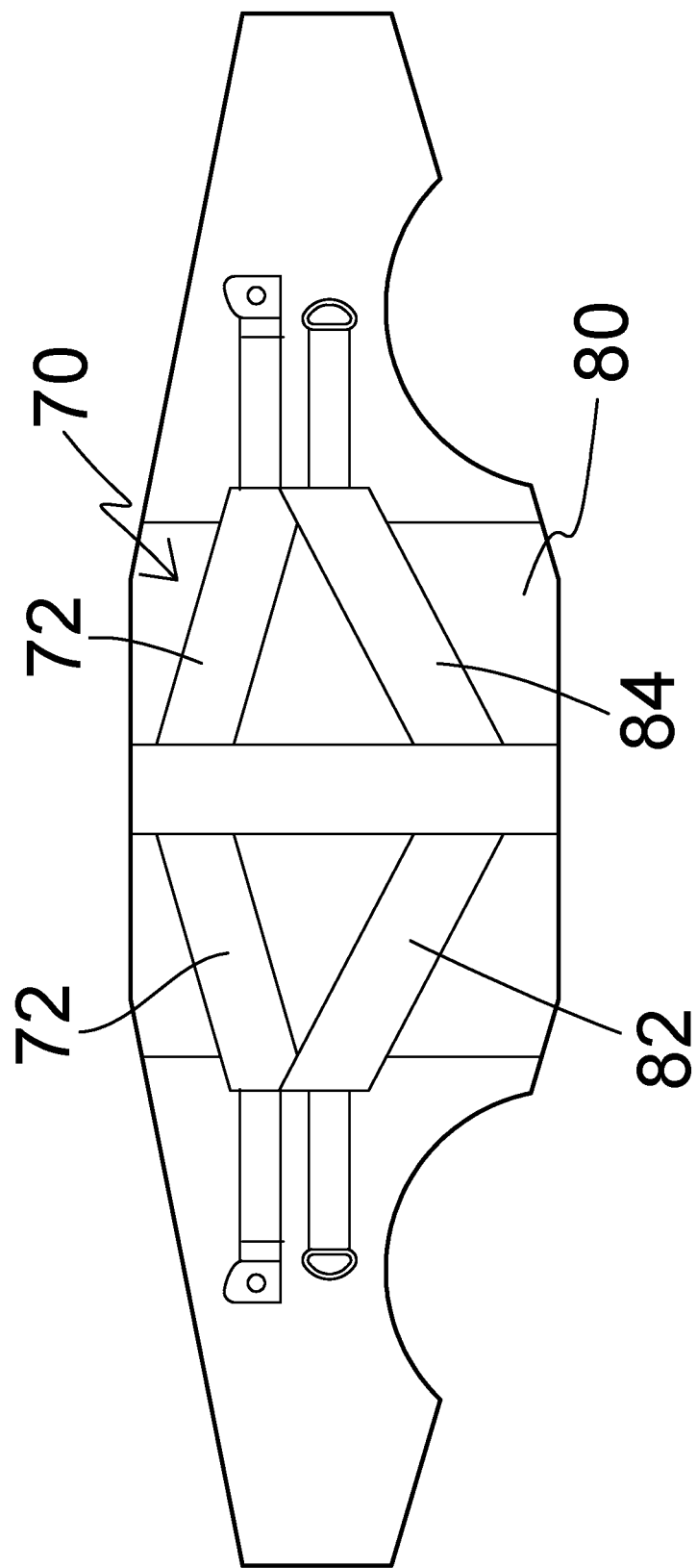
FIG. 3 is a front elevational view of a back support brace according to a first alternate configuration of the present invention.

The best mode for carrying out the invention is presented in terms of its preferred embodiment, herein depicted within the Figures. It should be understood that the legal scope of the description is defined by the words of the claims set forth at the end of this patent and that the detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term by limited, by implication or otherwise, to that single meaning. Finally, unless a claim element is defined by reciting the word "means" and a function without the recital of any structure, it is not intended that the scope of any claim element be interpreted based on the application of 35 U.S.C. § 112(f).

The best mode for carrying out the invention is presented in terms of its preferred embodiment, herein depicted within the Figures.

1. Detailed Description of the Figures

Referring now to the drawings, wherein like reference numerals indicate the same parts throughout the several views, a back support therapy brace, generally noted as 10, is shown according to the preferred embodiment of the present invention. The back support therapy brace 10 consists essentially of; a lower torso circumscribing band 12; and, a system of placeable and removable pressure nodules 30.

The lower torso circumscribing band 12 may be adapted to circumscribe a user's sacrum and lower back area. The band 12 may be formed of center panel 14 for overlaying against the sacrum and lower back. A left lateral extension strap 16 aligns a left terminus 14a of the center panel 14 and may form an extension thereof or be attached or affixed by a first seam 19. A right lateral extension strap 18 aligns a right terminus 14b of the center panel 14 and may form an extension thereof or be attached or affixed by a second seam 20. The center panel 14 and lateral straps 16, 18 may preferably formed from a semi-elastic material such as a neoprene that can be snugly fit to the wearer to offer support yet includes sufficient flexibility for wearer comfort both when standing, sitting and when performing activities such as lifting, etc.

The lateral straps 16, 18 are provided to circumscribe a wearer's torso and affix together so as to firmly hold the band 12 in place. While various types of attachment mechanisms may be used to secure the strap 16 to the strap 18, a hook and loop fastener system is preferred in which a hook fastener element 22 on the outside outermost portion of the left lateral strap 16 may secure to a functionally connecting loop fastener element 24 on the inside outermost portion of the right lateral strap 18. In this manner, the back brace 10 can be positioned with the center panel 14 positioned adjacent the wearer's back with the two retention straps 16, 18 extending outwardly from the center panel 14 in a manner to wrap around the wearer and attach in the front to retain the back brace 10 in position on the wearer.

In order to facilitate mobility of the user while being worn, each retention strap 16, 18 respectively forms a curvilinear profile recess 26 at a lower periphery. The formation of such a lower boundary allows the center panel 14 to be positioned lower upon a user's sacral region while minimizing impingement of motion on a wearer's hips.

As shown in conjunction with FIG. 4a through FIG. 6b, an exemplary system of placeable and removable pressure nodules 30 is depicted for use in conjunction with the back brace 10 for supporting a lower back region of a wearer. The system, generally noted as 30, includes placeable and removable pressure nodules that the wearer can place anywhere over the lower back and sacral region to provide precise pressure over muscles, tendon and connective tissue. As shown in FIG. 4a and FIG. 4b, a first nodule configuration 40 is shown forming a support 42 having a lower attachment surface 44. The lower attachment surface 44 is provided for removable attachment to the center panel 14 which includes a nodule attachment surface 35 at an inside face. While a number of removable attachment mechanism may be provide that are equivalently functional, a nodule attachment surface 35 formed of a planar face of loop portion of a hook and loop fastener material may be used to accommodate a lower attachment surface 44 formed of a hook portion of a hook and loop fastener material. The support 42 provides an offset 46 between the nodule attachment surface 35 and an impingement body 48. As shown in conjunction with FIG. 4a and FIG. 4b, the impingement body 48 is shown in a first size and shape, shown herein as a small hemispherical surface extending distally up from the offset 46.

It is intended that the various sizes, shapes and configurations of impingement bodies may be provided with different pressure nodule designs. By way of example, and not as a limitation, as shown in FIG. 5a and FIG. 5b, a second nodule configuration 50 is shown forming a support 52 having a lower attachment surface 54. The lower attachment surface 54 is provided for similar removable attachment to the nodule attachment surface 35. While a number of removable attachment mechanism may be provide that are equivalently functional, a nodule attachment surface 35 formed of a planar face of loop portion of a hook and loop fastener material may be used to accommodate a lower attachment surface 54 formed of a hook portion of a hook and loop fastener material. The support 52 provides an offset 56 between the nodule attachment surface 35 and an impingement body 58. As shown in conjunction with FIG. 5a and FIG. 5b, the impingement body 58 is shown in a second size and shape, shown herein as a large hemispherical surface extending distally up from the offset 56.

As shown in FIG. 6a and FIG. 6b, a third nodule configuration 60 is shown forming a support 62 having a lower attachment surface 64. The lower attachment surface 64 is provided for removable attachment to the center panel 14 which includes a nodule attachment surface 35 at an inside face. While a number of removable attachment mechanism may be provide that are equivalently functional, a nodule attachment surface 35 formed of a planar face of loop portion of a hook and loop fastener material may be used to accommodate a lower attachment surface 64 formed of a hook portion of a hook and loop fastener material. The support 62 provides an offset 66 between the nodule attachment surface 35 and an impingement body 68. As shown in conjunction with FIG. 6a and FIG. 6b, the impingement body 68 is shown in a third size and shape, shown herein as a rectangular block monolith surface extending distally up from the offset 66.

The system of placeable and removable pressure nodules 30 may include a plurality of various size and configuration of nodules including a various number of those in a first configuration 40, a second configuration 50 and a third configuration 60. It should be noted that the number of each size nodules, and the different types of size and configuration of nodules may vary and the described embodiments are meant merely as exemplary configurations and not as limiting or encompassing of such designs. These nodules can vary in size from ¾, inch in diameter, representing the size of the human finger to 4½ inches in diameter representing the size of the human palm. The length may vary from 1 inch to 3 inches to accommodate different body types. The density of the pressure nodules may vary from semi-soft, to rigid. The material may be open foam, such as EV or EVA, to a hard plastic material or wood. The larger nodule will be used for, but not limited to, the Quadratus lumborum (QL), which is responsible for pelvic stability and structural alignment. A second medium nodule will be used for, but not limited to, the Gluteus medius (GM), a muscle that frequently spasms and causes pain when the QL muscle is irritated. A smaller third nodule will be used for generalized trigger point therapy to other muscles that may be irritated.

In an intended use, as described in greater detail below, the present back brace 10 will provide a plurality of positionable and interchangeable nodules 40, 50, 60 in order to replicate a therapeutic effect similar to self-myofascial release (SMR) by providing pressure through the nodules onto myofascial points to relieve pain, increase flexibility and reduce connective tissue thickness. In order to provide further adaptation to facilitate such functionality, the belt 12 may be provided with a secondary tightening or cinching mechanism. Such a functionality may be provided by an upper binding strap 70 in which a laterally elongated member may be pulled outward and fastened in order to increase overall binding pressure about a user's body. Such a binding strap 70 may be of any functionally equivalent form, and is shown herein as a left strap element 72 and right strap element 74 that may be attached along the left strap 16 or right strap 18, respectively. Additionally, functionality may be further provided by a lower binding strap 80 in which a laterally elongated member may be pulled outward and fastened in order to increase overall binding pressure about a user's body. Such a binding strap 80 may be of any functionally equivalent form, and is shown herein as a left strap element 82 and right strap element 84 that may be attached along the left strap 16 or right strap 18, respectively.

2. Operation of the Preferred Embodiment

In operation the present back brace 10 has been modified and adapted to implement SMRT into the brace functionality by incorporating a system of placeable and removable pressure nodules. Through this system of nodules, the user can place the nodules anywhere over the lower back and sacral regions. This provides precise, specialized, and individualized pressure to the muscles, tendons, and connective tissues of each individual. Through this, the brace would decrease the need for the user to manually massage the area of pain. Such a system would leverage the user's own active motions—such as bending, twisting, or walking—to engage the muscles and massage the muscles with the pressure nodules. This type of therapy is similar to self-myofascial release (SMR) which is the utilization of pressure on myofascial points to relieve pain, increase flexibility and reduce connective tissue thickness. The present belt applies a pressure that is comfortable and determined by the individual to the affected area. Then with active motion, such as bending, twisting or walking, the muscle groups become engaged and are massaged by the pressure nodule. This gives the individual the above mentioned results. The belt will include unique pressure nodules which may have a design to interact with the different muscle groups of the back.

The present brace 10 may further include a strapping system, which the user can adjust to provide the desired pressure. To reduce pressure on the abdomen, this strapping system should be attached near the anterior hip region. This brace should provide an active cut designed to allow for freer motion of the hips and thighs, thus preventing the brace from riding up while the user is walking or sitting.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way. Any unintended embracement of such subject matter is hereby disclaimed.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents. Therefore, the scope of the invention is to be limited only by the following claims.

What is claimed is:

1. A back brace for providing self-myofascial release, comprising:
   a lower torso circumscribing band adapted to circumscribe a wearer's sacrum and lower back area and having
      a deformable center panel for overlaying the sacrum and lower back, the center panel having an inside face including a nodule attachment surface;
      a left lateral extension strap connected to a left terminus of the center panel and forming a first extension from the center panel;
      a right lateral extension strap connected to a right terminus of the center panel and forming a second extension from the center panel;
      wherein the left lateral extension strap and the right lateral extension strap are adapted to circumscribe the wearer's torso and affix together to hold the lower torso circumscribing band in place;
   a system of placeable and removable pressure nodules having a lower attachment surface attachable to any location on the nodule attachment surface of the center panel, wherein said system comprises a first pressure nodule and a second pressure nodule, wherein the first pressure nodule and the second pressure nodule both comprise:
      a support having the lower attachment surface for removable attachment to an inside face of said center panel;
      said support further providing an offset in distance between the nodule attachment surface and an impingement body; and
      said Impingement body terminating an apex of the support and extending distally up from the offset, wherein the first pressure nodule Impingement body has a shape that consists of a hemispherical surface and wherein the second pressure nodule impingement body i) has a hemispherical surface larger than the hemispherical surface of the first Pressure nodule impingement body or ii) has a shape that is a rectangular block monolith, thereby providing the first Pressure nodule with a different nodule shape configuration than the second pressure nodule, wherein the back brace further includes a secondary tightening mechanism, comprising:

an upper binding strap connected to a midpoint of the center panel and having a left strap element connected to the left lateral extension strap, and a right strap element connected to the right lateral extension strap, wherein the upper binding strap is independently adjustable as compared to the left lateral extension strap, the right lateral extension strap and a lower binding strap in order to increase binding pressure about the wearer's body, and the lower binding strap connected to a midpoint of the center panel and having a left strap element connected to the left lateral extension strap and a right strap element connected to the right lateral extension strap, wherein the lower binding strap Is independently adjustable as compared to the left lateral extension strap, the right lateral extension strap and the upper binding strap in order to Increase binding pressure about the wearer's body.

2. A back brace for Providing self-myofascial release, comprising:

a lower torso circumscribing band adapted to circumscribe a wearer's sacrum and lower back area and having a deformable center panel for overlaying the sacrum and lower back, the center panel having an inside face including a nodule attachment surface;

a left lateral extension strap connected to a left terminus of the center panel and forming a first extension from the center panel;

a right lateral extension strap connected to a right terminus of the center panel and forming a second extension from the center panel, wherein the left lateral extension strap and the right lateral extension strap are adapted to circumscribe the wearer's torso and affix together to hold the lower torso circumscribing band in place;

a system of placeable and removable pressure nodules having a lower attachment surface attachable to any location on the nodule attachment surface of the center panel, wherein said system comprises a first pressure nodule and a second pressure nodule, wherein the first pressure nodule and the second pressure nodule both comprise:

a support having the lower attachment surface for removable attachment to an inside face of said center panel;

said support further providing an offset in distance between the nodule attachment surface and an impingement body; and said impingement body terminating an apex of the support and extending distally up from the offset, wherein the first pressure nodule impingement body has a shape that consists of a hemispherical surface and wherein the second pressure nodule impingement body i) has a hemispherical surface larger than the hemispherical surface of the first pressure nodule impingement body or ii) has a shape that is a rectangular block monolith, thereby providing the first pressure nodule with a different nodule shape configuration than the second pressure nodule and wherein said center panel, said left lateral extension strap, and said right lateral extension strap are formed from a semi-elastic material;

wherein the back brace further includes an upper binding strap connected to a midpoint of the center panel and having a left strap element connected to the left lateral extension strap, and a right strap element connected to the right lateral extension strap, wherein the upper binding strap is independently adjustable as compared to the left lateral extension strap, the right lateral extension strap and a lower binding strap in order to increase binding pressure about the wearer's body, and the lower binding strap connected to a midpoint of the center panel and having a left strap element connected to the left lateral extension strap and a right strap element connected to the right lateral extension strap, wherein the lower binding strap is independently adjustable as compared to the left lateral extension strap, the right lateral extension strap and the upper binding strap in order to increase binding pressure about the wearer's body.

3. The back brace according to claim 1, wherein the second pressure nodule has a shape that is the rectangular block monolith.

* * * * *